(12) United States Patent
Messora

(10) Patent No.: US 8,343,557 B2
(45) Date of Patent: Jan. 1, 2013

(54) COMPOSITIONS INCORPORATING AGENTS FOR REDUCING CELLULITE AND UNAESTHETIC APPEARANCE ASSOCIATED THEREWITH AND FORMULATIONS CONTAINING THEM

(75) Inventor: Edoardo Messora, Cascais (PT)

(73) Assignee: STARGATE—Produtos Farmacêuticos, Dietéticos e Nutricionais, Lda., Amadora (PT)

( * ) Notice: Subject to any disclaimer, the term of this patent is extended or adjusted under 35 U.S.C. 154(b) by 169 days.

(21) Appl. No.: 12/606,700

(22) Filed: Oct. 27, 2009

(65) Prior Publication Data

US 2010/0278908 A1   Nov. 4, 2010

(30) Foreign Application Priority Data

Oct. 29, 2008   (PT) ........................................ 104241

(51) Int. Cl.
- *A61K 36/87* (2006.01)
- *A61K 36/15* (2006.01)
- *A61K 36/82* (2006.01)
- *A61K 31/715* (2006.01)
- *A01N 37/00* (2006.01)

(52) U.S. Cl. ........ 424/766; 424/770; 424/729; 424/776; 424/775; 424/637; 514/558; 514/560; 514/54; 514/167; 514/62

(58) Field of Classification Search .................. None
See application file for complete search history.

(56) References Cited

U.S. PATENT DOCUMENTS

| | | | |
|---|---|---|---|
| 6,676,977 B2 * | 1/2004 | Murad | |
| 6,875,754 B1 * | 4/2005 | Griesbach et al. | |
| 2001/0041708 A1 | 11/2001 | Halvorsen et al. | |

FOREIGN PATENT DOCUMENTS

| | | | |
|---|---|---|---|
| EP | 1214048 | | 6/2002 |
| EP | 1663267 | | 6/2006 |
| FR | 2674126 A1 * | | 9/1992 |
| JP | 11071294 A * | | 3/1999 |
| JP | 2003277223 A * | | 10/2003 |
| WO | WO 0117498 A1 * | | 3/2001 |
| WO | WO 03/006009 | | 1/2003 |

OTHER PUBLICATIONS

Matsen, S. (Aug. 13, 2005). "Fighting Cellulite and Winning." Retrieved Oct. 2, 2011, from http://ezinearticles.com/?Fighting--Cellulite--and--Winning&id=59822.*

Dweck, AC. New Ideas from the shows and exhibitions of 2005/2006. A Personal Care Magazine Special. Downloaded from www Oct. 2, 2011. http://liveweb.archive.org/http://www.dweckdata.com/Published_papers/NewIdeas2006.pdf.*

* cited by examiner

*Primary Examiner* — Michele C. Flood
(74) *Attorney, Agent, or Firm* — Pearl Cohen Zedek Latzer, LLP

(57) ABSTRACT

The present invention relates to synergic compositions incorporating agents for reducing cellulite and unaesthetic appearance associated therewith which comprise a base matrix constituted by conjugated linoleic acid (CLA), grape seed extract, beta-glucan, organic calcium and dry extract of pine bark together with complementary synergic agents of the matrix. The invention also relates to the use of such compositions and formulations containing said compositions.

7 Claims, No Drawings

COMPOSITIONS INCORPORATING AGENTS FOR REDUCING CELLULITE AND UNAESTHETIC APPEARANCE ASSOCIATED THEREWITH AND FORMULATIONS CONTAINING THEM

FIELD OF THE INVENTION

The present invention relates to synergic compositions for the treatment of cellulite and related disorders and formulations using such compositions.

BACKGROUND OF THE INVENTION

To date, it has been accepted that cellulite, not being considered exactly an autoimmune syndrome, presents some aspects that explain the difficulty in removing it. The presence of fat tissue deposits in women is controlled by DNA, and these deposits are not removed by traditional diet methods or through the ingestion of draining liquids. In order for methods external to the organism to reduce the phenomenon of cellulite, which is internal to the organism, it is necessary that the fat molecules contained within the cells leave their protective film, i.e. the adipocytes. For this process to occur from the inside, it is necessary to destroy this protective film, removing the fat particles, which can be eliminated osmotically through an appropriate drainage, or additionally by the mechanical action of a specific massage, performed with cream and activated oil.

Cellulite is certainly not a serious condition, from a medical point of view, but it represents the most common and least tolerated aesthetic complaint among women. Cellulite is a physiological condition classified as a microcirculatory dysfunction of the endocrine metabolism. It is characterized by skin depression, volume and deformation, i.e. "skin ripples", which give it its distinctive appearance. Although cellulite is the common term for this disorder, it would be more correct, in clinical terms, to use names such as edematous fibrosclerotic panniculopathy, gynoid hydrolipodystrophy or simply lipodystrophy.

Cellulite appears in young women shortly after the menarche in the thighs and buttocks and continues to worsen as times goes by. The process of cellulite formation can be divided into 4 phases:

1—Arteriolar precapillary sphincter changes leading to changes in vascular permeability and capillary dilation resulting in edema.
2—Edema, causing metabolic changes which result in reticular plexus hyperplasia and hypertrophy, leading to pericapillarity formation and adipocyte deposition, and increasing interstitial viscosity.
3—Organization of collagen fibers around adipocyte groups, forming micronodules.
4—Finally, there is a union of micronodules forming macronodules and leading to sclerosis.

There are many factors causing cellulite and many others which aggravate it. Several factors should be highlighted, including obesity and overweight, hormone ingestion, anatomical changes interfering with the normal metabolic processes and with microcirculation, nutritional deficiencies and metabolic disorders.

Many cellulite treatments exist, which include numerous processes that can only be applied in specific centers by professionals.

In cosmetic terms, an important weapon is massage itself. The anti-cellulite massage alone can stimulate microcirculation, facilitating metabolic changes and helping at least to prevent cellulite from developing quickly and easily. Massage therapy itself reduces tissue edema, but effects are also likely to be noticed at cellular level, since it stimulates fibroblast and keratinocyte activity, and reduces adipocyte activity.

The active ingredients used in cosmetics and in supplementary integration are essentially the same, depending on their technological characteristics, but generally they belong to the same therapeutic groups, of which we can enumerate agents that increase blood flow, agents that reduce lipogenesis and promote lipolysis, agents that restore the normal structure of the dermis and subcutaneous tissue and agents that prevent or eliminate the formation of free radicals.

European patent application EP 1214048 shows the use of conjugated linoleic acid (CLA) for the treatment and prevention of fat deposits and cellulite and compositions thereof containing CLA for the treatment of these disorders.

U.S. patent application US 20010041708 discloses a method to combat cellulite by applying a composition containing 10-trans, 12-cis-CLA.

The publication of international patent application WO 03/006009 relates to compositions for preventing cellulite containing CLA, an imidazolic or triazolic antifungal agent and a vehicle.

European patent application EP 1663267 relates to oral pharmaceutical compositions and cosmetic compositions for treating cellulite containing standardized extract of *Vitis vinifera*, dimeric flavonoids of *Ginkgo biloba* and triterpenes from *Centella asiatica*.

DETAILED DESCRIPTION OF THE INVENTION

The present invention relates to synergic compositions that are highly effective in the treatment of cellulite and the unaesthetic symptoms related to it.

A first object of the invention are compositions incorporating agents for reducing cellulite and unaesthetic appearance associated therewith, which comprise:
  a) A base matrix constituted by conjugated linoleic acid (CLA), grape seed extract, beta-glucan, organic calcium and dry extract of pine bark; and
  b) Complementary synergic agents of the matrix, selected from riboflavin, folic acid, vitamin D3, biotin, copper sulfate, glucosamine sulfate and dry extract of *Camellia sinensis* (95%).

In a preferred embodiment, the matrix is constituted by linoleic acid conjugated to 80%, standardized extract of grape seed, *Vitis vinifera*, to 95% beta-glucan of *Saccharomyces cerevisiae* to 85%, organic calcium of plant origin and with high bioavailability (calcium from *Lithothamnium* spp.) to 32% and dry extract of pine bark (*Pinus massoniana*) to 95%.

Only through the combined action of the matrix and the complementary agents is it possible to obtain real results (reduction of one or more degrees of real cellulite) during each treatment cycle (90 days). The compositions of the invention are synergic and their effects are much greater than would be expected from their individual components.

The contribution of each matrix component is as follows:
Conjugated Linoleic Acid Conjugated linoleic acid (CLA) has snumerous biological properties, including its effects on lipid metabolism and on body and milk composition.

Conjugated linoleic acid (CLA) is a collective term used to describe a group of positional and geometric isomers of linoleic acid. These compounds can be produced naturally by hydrogenation and bacterial isomerization in the intestine of ruminant animals or they can be produced chemically by alkaline isomerization of linoleic acid.

In fact, the presence of CLA has been associated with a decreased risk of cancer induced by chemical agents in animal studies. Furthermore, CLA appears to have anti-atherogenic properties by reducing total cholesterol and LDL-cholesterol, as well as influencing body composition by reducing fat deposition and increasing lean body mass. There is also evidence that suggests anti-thrombotic properties of the CLA in concentrations similar to the ones found in food. The various effects of CLA appear to be mediated by the action on plasma transport and on the lipid metabolism, lipid peroxidation and prostaglandin biosynthesis.

Conjugated linoleic acid appears to have two major sites of action: fat cells or adipocytes (which store fat) and skeletal muscle cells (where fat is used for energy production).

Based on laboratory and clinical studies, conjugated linoleic acid works by reducing fat body mass in 4 ways:
  Increasing fat degradation rate in the fat cells
  Increasing degradation mechanism rate
  Reducing the amount of fat stored after eating
  Reducing the total number of fat cells Together, these mechanisms lead to a decrease in both the number and size of fat cells, thus reducing fat body mass.

Dry Extract of Grape Seed (*Vitis vinifera*)

Dry grape seed extract (95%) is used for therapeutic purposes, being rich in procyanidins, antocyanidins and leucoantocyanidins (catechin and epicatechin derivatives), both members of the flavonoid family. The action of *Vitis vinifera* is due to the fact of promoting the reduction of blood pressure by inhibiting the enzyme that converts angiotensin I to II; this leads to an improvement of chronic venous insufficiency, as evidenced by the improvement of associated symptoms (paraesthesia and pain) and objective improvement of aesthetic factors related to vascular insufficiency. It also decreases platelet aggregation and exerts a powerful antioxidant effect due to its free radical scavenging action, in particular by its ability to capture superoxide and hydroxyl radicals and thus inhibit lipid peroxidation. These antioxidant properties reinforce the anti-inflammatory effects and the antiprotease capacity, inhibiting elastic fibers and thus protecting the membranes of the endothelial cells. Regarding lipid metabolism, antioxidant capacities increase high-density lipoprotein (HDL) plasma concentration, reduce total cholesterol and low density lipoproteins (LDL). It also has anti-anemic, alkalizing, mineralizing, diuretic, purgative, anti-inflammatory and soothing actions.

Its proposed indications are recovery from deep scars, dry skin protection and stretch mark prevention, improvement of chronic venous insufficiency, capillary fragility, hypertension and others.

Beta-Glucan

Chemically, beta-glucan is a long molecule—a polymer—formed by units that repeat themselves about 1400 times, in this case glucose or glucopyranose, an enclosed structure or a ring with six carbons. When isolated it is a sugar soluble in hot water, forming a clear solution; when interacting with other molecules, beta-glucan forms suspended particles. Beta-glucan, even at low concentrations, can reduce the blood glucose level by up to 50%. It is an immunostimulant extracted from the cell walls of beer yeast. Beta-glucan activates white blood cells, such as macrophages, granulocytes and monocytes, which are responsible for defense against infections, and it helps in the repair of degenerated tissues since it stimulates the regeneration process. Beta-glucan is a polysaccharide that triggers the modulation action of the immune system, increases T and B lymphocyte and macrophage activity, enhancing the natural defenses against virus infections, bacteria, fungi, parasites and tumor cells.

Organic Calcium of Plant Origin (*Lithothamnium* spp.)

It is a source of calcium of plant origin, with the following advantages:
  Natural source of minerals
  100% plant Derived
  Lactose-free
  Imperceptible flavor
  Unique porous structure
  Superior organoleptic properties, when compared with other sources of calcium This form of organic calcium contains over 70 minerals, including, in addition to calcium, the following: Magnesium, Phosphorus, Sulfur, Iron, Boron, Fluorine, Selenium, Cobalt, Copper, Zinc, Sodium, Molybdenum, Iodine, Manganese and Nickel.

Extract of Pine Bark

The Pine bark has a high content of OPCs (oligomeric proanthocyanidins). It has been determined that OPCs have a high antioxidant power, being non-toxic, non-mutagenic, non-carcinogenic, and not having reported secondary effects. The antioxidant capacity of pine bark comes from the OPCs, with an antioxidant power of about 20 times that of vitamin C and 50 times greater than that of Vitamin E. OPCs are a recognized antioxidant that neutralize free radicals, which in turn have a key role in degenerative and cardiovascular diseases, eye diseases, premature aging, etc.

Several studies have confirmed that OPCs help to strengthen capillaries, arteries and veins, which allows numerous clinical applications of vital importance. OPCs apparently stabilize the walls of blood vessels, reduce inflammation, and generally support tissues that contain collagen and elastin. By strengthening capillarity and reducing capillary osmosis, OPCs may relieve pain and edemas associated with venous insufficiency. OPCs accelerate the disappearance of edema, by strengthening blood and lymph vessels that are damaged and causing dysfunction in their flows. OPCs protect and accelerate skin collagen and elastin.

In a more preferred embodiment, the matrix of the composition of the present invention comprises from 5 to 50% linoleic acid conjugated to 80%, from 0.5 to 5% standardized extract of grape seed, *Vitis vinifera*, to 95%, 0.2 to 2% of beta-glucan of *Saccharomyces cerevisiae* to 85%, from 3 to 30% organic calcium of plant origin with high bioavailability (calcium from *Lithothamnium* spp.) to 32% and from 0.2 to 3% dry extract of pine bark (*Pinus massoniana*) to 95%.

A second object of the invention is the use of compositions of the present invention in the production of formulations for the treatment of cellulite and unaesthetic appearance associated therewith.

A third object of the invention are formulations for the treatment of cellulite and unaesthetic appearance associated therewith, which comprise the compositions of the invention, along with appropriate vehicles and excipients.

Typically, the formulations of the invention are presented in the form of soft gelatin capsules, hard gelatin capsules, sachets for oral solutions, massage creams and massage oils.

Preferably, the formulations of the invention comprise 100 to 2500 mg of linoleic acid conjugated to 80%, from 10 to 1000 mg standardized extract of grape seed, *Vitis vinifera*, to 95%, from 1 to 1000 mg beta-glucan *Saccharomyces cerevisiae* to 85%, from 50 to 1250 mg organic calcium of plant origin with high bioavailability (calcium from *Lithothamnium* spp.) to 32% and 2.5 to 500 mg dry extract of pine bark (*Pinus massoniana*) to 95%.

More preferably, the formulations of the invention comprise 250 to 1500 mg of linoleic acid conjugated to 80%, from 25 to 250 mg standardized grape seed extract, *Vitis vinifera*, to 95%, from 2.5 to 50 mg beta-glucan of *Saccharomyces cerevisiae* to 85%, from 100 to 750 mg organic calcium of plant origin with high bioavailability (calcium from *Lithothamnium* spp.) to 32% and from 5 to 250 mg dry extract of pine bark (*Pinus massoniana*) to 95%.

A fourth object of the invention is the use of the compositions of the invention in the production of hard gelatin capsules with a liquid filling system, yoghurts, milk drinks and fruit juices.

Formulations

The formulations of the present invention allow a combined action of the key components of the product, in particular the matrix components.

The application of the formulations of the present invention allows a comprehensive approach to the problem of cellulite, also having a slimming action that occurs in parallel to the treatment of cellulite.

The formulations are presented in various forms, as mentioned above, for example the following:
- Food supplement, soft gelatin capsules.
- Food supplement, sachets of soluble powder to dissolve in water.
- Anti-cellulite and slimming cream—Cosmetic, tube of cream to be applied in the affected areas.
- Cosmetic, tube of massage oil to be applied after the cream to the affected areas.

The soft gelatin capsule formulation is not the only one that can be chosen, but it is certainly the most practical to be easily ingested and with a high rate of adherence to the therapy for each user, in particular because it allows the administration of CLA in its most bioavailable form.

The composition of the present invention may also be included in the composition of hard gelatin capsules with a liquid filling system, yoghurt and milk drinks and fruit juices and other beverages.

EXAMPLES

The following tables describe some examples of the formulation of the invention:

Example 1

Soft Gelatin Capsules (2 Per Day)

| Ingredients | Quantity per capsule | % |
|---|---|---|
| Conjugated linoleic acid (CLA) | 500 mg | 31.9 |
| Edible gelatin | 303.8 mg | 19.4 |
| Acquamin TG ® (calcium from *Lithothamnium* spp.) | 300 mg | 19.15 |
| Glycerol | 140 mg | 8.94 |
| Glucosamine sulfate | 100 mg | 6.39 |
| Green tea [*Camellia sinensis* (L.) O. Kuntze, dry leaf extract, maltodextrins] | 75 mg | 4.80 |
| Vine (*Vitis vinifera*, dry extract of grape seed) | 50 mg | 3.19 |
| Polyglycerol oleate | 30 mg | 1.92 |
| Pine (*Pinus massoniana*, dry extract of bark) | 22.5 mg | 1.44 |
| Glyceryl monostearate | 15 mg | 0.96 |
| Beta-glucan (Beta-glucan of *Saccharomyces cerevisiae*) | 11.17 mg | 0.72 |
| Emulsifier: Soya lecithin (soya lecithin, soybean oil) | 10 mg | 0.64 |
| Colorant: E 171 | 5.01 mg | 0.32 |
| Cupric sulfate | 1.506 mg | 0.10 |
| Vitamin B2 (Riboflavin) | 1.32 mg | 0.08 |
| Colorant: E 122 | 0.350 mg | 0.02 |
| Folate (Pteroylmonoglutamic acid) | 0.18 mg | 0.01 |
| Vitamin D3 (Cholecalciferol, coconut oil) | 0.18 mg | 0.01 |
| Biotin (D-biotin) | 0.135 mg | 0.01 |

Example 2

Hard Gelatin Capsules with Microgranules Incorporating the Liquid Matrix (4 Per Day)

| Ingredients | Quantity per capsule | % |
|---|---|---|
| Conjugated linoleic acid (CLA) | 250 mg | 31.9 |
| Fatty acid monodiglycerides | 110.5 mg | 14.11 |
| Acquamin TG ® (calcium from *Lithothamnium* spp.) | 150 mg | 19.15 |
| Microcrystalline cellulose | 70.94 mg | 9.06 |
| Glucosamine sulfate | 50 mg | 6.39 |
| Green tea [*Camellia sinensis* (L.) O. Kuntze, dry leaf extract, maltodextrins] | 37.5 mg | 4.8 |
| Vine (*Vitis vinifera*, dry extract of grapes seeds) | 25 mg | 3.19 |
| Dicalcium fosfate | 66.32 mg | 8.47 |
| Pine (*Pinus massoniana*, dry extract of bark) | 11.25 mg | 1.44 |
| Silicon dioxide | 4.39 mg | 0.56 |
| Beta-glucan (Beta-glucan of *Saccharomyces cerevisiae*) | 5.58 mg | 0.72 |
| Magnesium stearate | 4.39 mg | 0.56 |
| Cupric sulfate | 0.753 mg | 0.10 |
| Vitamin B2 (Riboflavin) | 0.66 mg | 0.08 |
| Folate (Pteroylmonoglutamic acid) | 0.09 mg | 0.01 |
| Vitamin D3 (Cholecalciferol, coconut oil) | 0.09 mg | 0.01 |
| Biotin (D-Biotin) | 0.068 mg | 0.01 |
| Gelatine capsule | 95 mg | |

Example 3

Oral Solution (1 Sachet Per Day)

| Ingredients | Quantity per dose (10 ml) | % |
|---|---|---|
| Fructose | 3740.16 mg | 31.168 |
| Demineralized water | 4200 mg | 35 |
| Maltodextrins | 1800 mg | 15 |
| Conjugated linoleic acid (CLA) | 1000 mg | 8.33 |
| Acquamin TG ® (Calcium from *Lithothamnium* spp.) | 600 mg | 5 |
| Flavoring | 18 mg | 0.15 |
| Citric acid | 61.2 mg | 0.51 |
| Glucosamine sulfate | 200 mg | 1.7 |
| Green tea [*Camellia sinensis* (L.) O. Kuntze, dry leaf extract, maltodextrins] | 150 mg | 1.25 |
| Vine (*Vitis vinifera*, dry extract of grape seed) | 100 mg | 0.83 |
| Xanthan gum | 12 mg | 0.1 |
| Pine (*Pinus massoniana*, dry extract of bark) | 45 mg | 0.375 |
| Potassium sorbate | 8.4 mg | 0.07 |
| Sodium benzoate | 8.4 mg | 0.07 |
| Beta-glucan (Beta-glucan of *Saccharomyces cerevisiae*) | 44.68 mg | 0.372 |
| Colorant: E 124 | 2.4 mg | 0.02 |
| Cupric sulfate | 3 mg | 0.025 |
| Vitamin B2 (Riboflavin) | 2.64 mg | 0.022 |
| Folate (Pteroylmonoglutamic acid) | 0.36 mg | 0.003 |

-continued

| Ingredients | Quantity per dose (10 ml) | % |
|---|---|---|
| Vitamin D3 (Cholecalciferol, coconut oil) | 0.36 mg | 0.003 |
| Biotin (D-biotin) | 0.272 mg | 0.002 |

Example 4

Massage Cream (1, 2 Times Per Day)
Active Compounds:
Conjugated linoleic acid 0.5%, standardized extract of grape seed, *Vitis vinifera* 0.5%, beta-glucan of *Saccharomyces cerevisiae* 0.3%, organic calcium of plant origin with high bioavailability, Acquamin TG® calcium from *Lithothamnium* spp.) 0.5%, pine (*Pinus massoniana*, dry extract of bark) 0.5%.

| INCLUDES | Functionality |
|---|---|
| Water | solvent |
| C12-20acid PEG-8 ester | surfactant-emulsifying agent |
| Glycerin | skin conditioning agent-humectant |
| Cetearyl ethylhexanoate | Skin conditioning agent-emollient |
| Isostearyl avocadate | Skin conditioning agent-emollient |
| PEG-6 Isostearate | surfactant-cleaning agent |
| Butylene glycol | skin conditioning agent-miscellaneous |
| Conjugated linoleic acid | skin conditioning agent-miscellaneous |
| *Vitis vinifera*, seed extract | skin conditioning agent-miscellaneous |
| *Saccharomyces cerevisae* (beta-glucan) | not mentioned |
| Caffeine | skin conditioning agent-miscellaneous |
| *Lithothamnium* spp. | skin conditioning agent-miscellaneous |
| Extract of *Pinus massoniana* | not mentioned |
| Extract of *Ananas sativus* | not mentioned |
| Propylene glycol | skin conditioning agent-miscellaneous |
| Isopropyl isostearate | skin conditioning agent-emollient |
| Dimethicone | skin conditioning agent-occlusive |
| Cyclopentasiloxane | Skin conditioning agent-emollient |
| Carbomer | Emulsion stabilizer |
| Triethanolamine | pH adjuster |
| Polysorbate 80 | surfactant-emulsifying agent |
| Dipropylene glycol | solvent |
| Perfume | fragrant ingredient |
| Benzyl alcohol | fragrant ingredient |
| Tocopherol | antioxidant |
| BHT | fragrant ingredient |
| Phenoxyethanol | preservative |
| Potassium sorbate | preservative |
| Methylparaben | preservative |
| Ethylparaben | preservative |
| Alcohol | solvent |
| Isobutylparaben | preservative |
| Propylparaben | preservative |
| Butylparaben | preservative |
| CI 19140 | Colorant |
| CI 42090 | Colorant |
| Benzophenone-4 | sunscreen protection agent |

Use
The composition of the present invention allows a much higher reduction of cellulite and related unaesthetic phenomena than could be achieved from the sum of the effects obtained from the separate administration of the single components of the association, understandably due to the synergy between the components. The compositions of the present invention are preferably ingested during the main meals, a total of 2 daily doses. The compositions of the present invention may be formulated in a form appropriate for oral administration and will be prepared according to conventional methods universally recognized in pharmaceutical technique, such as those described in Remington's Pharmaceutical Handbook, Mack Publishing Co. NY, USA, using suitable solvent excipients and other co-formulants appropriate for their end use.

All the formulations of the present invention combat cellulite in its various stages.

Cellulite is technically classified into several aesthetic stages:

Stage 0—In a standing position, the skin on the thighs and buttocks has a smooth surface. When doing the pinch test, there is no dimpling.

Stage I—In a standing position, smooth skin, but the pinch test shows volume and depression.

Stage II—Smooth skin when lying down, but there is deformation and volume in the standing position. This stage is very common in women over the age of 35/40 years.

Stage III—The state of deformation or increased volume is visible regardless of whether standing or lying down. It is common in menopausal and obese women.

In clinical application experiments it was concluded that the formulations of the present invention allow:

The reduction of the intensity of the cellulite phenomenon, by at least 1 degree, even reaching 2 degrees, in a course of treatment which corresponds to 3 months.

Reduction in overall fat mass, and slimming of the lower body (flank, buttocks and legs) and also the arms and belly.

Reduction of the diameter of the thighs and epidermal adjustment.

Toning and elasticity of the skin.

Those who prefer, having practically achieved the goal of reducing cellulite after the first treatment, can repeat it in full, in the case of a high degree of cellulite intensity which requires another complete cycle. There is also the possibility of using one or more types of formulation of the present invention, if the progress obtained after the first cycle of treatment are so requires:

Capsules+Draining agent
Capsules Massage Cream+Massage Oil
Capsules
Only Drainage Therapy Massage Cream Draining Oil.

The invention claimed is:

1. An oral composition incorporating an agent for reducing cellulite and unaesthetic appearance associated therewith, wherein the agent comprises: a) a base matrix comprising conjugated linoleic acid (CLA), grape seed extract, beta-glucan from *Saccharomyces cerevisiae*, organic calcium from *Lithothamnium* spp. and dry extract of pine bark; and b) additional agents comprising 1-5 mg riboflavin, 0.1-0.5 mg folic acid, 0.1-0.5 mg vitamin D3, 0.1-0.5 mg biotin, 1-5 mg copper sulfate, 50-100 mg glucosamine sulfate and dry extract of *Camellia sinensis* L.

2. The oral composition according to claim 1, wherein the matrix comprises conjugated linoleic acid; grape seed extract from *Vitis vinifera* L.; beta-glucan from *Saccharomyces cerevisiae*; organic calcium of plant origin from *Lithothamnium* spp.; and pine bark from *Pinus massoniana* L.

3. The oral composition according to claim 1, wherein the matrix comprises from 5 to 50% of conjugated linoleic acid; from 0.5 to 5% of grape seed extract from *Vitis vinifera* L.; from 0.2 to 2% of beta-glucan from *Saccharomyces cerevisiae*; from 3 to 30% of organic calcium of plant origin from *Lithothamnium* spp.; and from 0.2 to 3% of dry extract of pine bark from *Pinus massoniana* L.

4. An oral formulation for the treatment of cellulite and unaesthetic appearance associated therewith, comprising the oral composition of claim 1 and a pharmaceutically acceptable excipient.

5. The formulation according to claim 4, prepared in the form of a soft gelatin capsule, a hard gelatin capsule, a sachet for oral solutions, a massage cream or a massage oil.

6. The oral formulation according to claim 4, comprising from 100 to 2500 mg of conjugated linoleic acid; from 10 to 1000 mg of grape seed extract from *Vitis vinfera* L.; from 1 to 1000 mg of beta-glucan from *Saccharomyces cerevisiae*; from 50 to 1250 mg of organic calcium of plant origin from *Lithothamnium* spp.; and from 2.5 to 500 mg of dry extract of pine bark from *Pinus massoniana* L.

7. The oral formulation according to claim 6 comprising from 250 to 1500 mg of conjugated linoleic acid; from 25 to 250 mg of grape seed extract from *Vitis vinifera* L.; from 2.5 to 50 mg of beta-glucan from *Saccharomyces cerevisiae*; from 100 to 750 mg of organic calcium of plant origin from *Lithothamnium* spp.; and from 5 to 250 mg of dry extract of pine bark from *Pinus massoniana* L.

* * * * *